(12) United States Patent
O'Rourke et al.

(10) Patent No.: US 11,810,410 B2
(45) Date of Patent: Nov. 7, 2023

(54) CONTACTLESS DELIVERY LOCKER SYSTEM

(71) Applicant: BRGHTLY INC., Malibu, CA (US)

(72) Inventors: David O'Rourke, Malibu, CA (US);
Adam O'Rourke, Malibu, CA (US);
Dennis Draleau, Lehi, UT (US);
Michele Kay Schuster, Malibu, CA (US)

(73) Assignee: BRGHTLY INC., Malibu, CA (US)

( * ) Notice: Subject to any disclaimer, the term of this patent is extended or adjusted under 35 U.S.C. 154(b) by 0 days.

(21) Appl. No.: 17/561,914

(22) Filed: Dec. 24, 2021

(65) Prior Publication Data

US 2022/0122389 A1    Apr. 21, 2022

Related U.S. Application Data

(63) Continuation of application No. 16/938,961, filed on Jul. 25, 2020, now abandoned.

(51) Int. Cl.
*G07C 9/00* (2020.01)
*A61L 2/26* (2006.01)
(Continued)

(52) U.S. Cl.
CPC ....... *G07C 9/00182* (2013.01); *A47G 29/141* (2013.01); *A61L 2/10* (2013.01);
(Continued)

(58) Field of Classification Search
CPC .............. G07C 9/00182; A47G 29/141; A47G 2029/142; A47G 2029/147; A47G 2029/149; A61L 2/10; A61L 2/26
See application file for complete search history.

(56) References Cited

U.S. PATENT DOCUMENTS 10,424,143 B2   9/2019   Miller et al.
2005/0080689 A1   4/2005   Liberman
(Continued)

FOREIGN PATENT DOCUMENTS

EP    3550487 A1    10/2019
WO    2014125243 A1    8/2014

OTHER PUBLICATIONS

Food Delivery, 7 pgs, Wikipedia, retrieved Jul. 2, 2020 from https://en.wikipedia.org/wiki/Food_delivery.
(Continued)

*Primary Examiner* — Nabil H Syed
(74) *Attorney, Agent, or Firm* — Mark E. Ungerman; Ungerman IP PLLC

(57) ABSTRACT

A contactless delivery locker may have a locker housing with a locker door fitted to the locker housing. A disinfecting system may be arranged to disinfect the locker content and a remotely actuable lock may be arranged to secure the locker door in a closed position and actuable to release the locker door. A controller associated with the lock may be configured to actuate the lock and a wireless interface may be connected to the controller and configured to receive a command to actuate the lock to release the locker door. The controller may operate to control actuation of the lock to release the locker door upon detection of a command to actuate the lock and release the locker door. The controller may be configured to report lock status information to a user to confirm if a locker has been opened after completion of a disinfecting cycle.

16 Claims, 4 Drawing Sheets

(51) Int. Cl.
*A61L 2/10* (2006.01)
*A47G 29/14* (2006.01)

(52) U.S. Cl.
CPC .......... *A61L 2/26* (2013.01); *A47G 2029/142* (2013.01); *A47G 2029/147* (2013.01); *A47G 2029/149* (2013.01); *A61L 2202/11* (2013.01); *A61L 2202/121* (2013.01); *A61L 2202/122* (2013.01); *A61L 2202/14* (2013.01); *A61L 2202/23* (2013.01)

(56) References Cited

U.S. PATENT DOCUMENTS

| | | |
|---|---|---|
| 2011/0020175 A1 | 1/2011 | Collard et al. |
| 2012/0153783 A1 | 6/2012 | Shoenfeld |
| 2018/0084959 A1 | 3/2018 | Hall et al. |
| 2018/0207307 A1 | 7/2018 | Schwartz et al. |
| 2018/0242768 A1 | 8/2018 | Lewis |
| 2020/0066086 A1 | 2/2020 | Fee et al. |
| 2020/0234016 A1 | 7/2020 | Chen et al. |
| 2020/0237119 A1 | 7/2020 | Jakubowski et al. |
| 2020/0237946 A1 | 7/2020 | Shell et al. |

OTHER PUBLICATIONS

Nicole Pajer, Is It Safe To Order Takeout During The Coronavirus Outbreak?, Food & Drink, Mar. 17, 2020, 13 pgs, Huffington Post, retrieved Jul. 2, 2020 from https://www.huffost.com/entry/coronavirus-takeout-safe-tips.

Sarwant Singh, The Soon To Be $200B Online Food Delivery Is Rapidly Changing The Global Food Industry, Sep. 9, 2019, 7 pgs, Forbes, retrieved Jul. 2, 2020 from https://www.forbes.com/sites/sarwantsingh/2019/09/09/the-soon-to-be-$200B-online-food-delivery-is-rapidly-changing-the-global-food-industry.

Take Out, 9 pgs, Wikipedia, retrieved Jul. 2, 2020 from https://en.wikipedia.org/wiki/take-out.

Ultraviolet germicidal irradiation, 12 pgs, Wikipedia, retrieved Jul. 2, 2020 from https://en.wikipedia.org/wiki/ultraviolet_germicidal_irradiation.

CONTACTLESS DELIVERY LOCKER SYSTEM

CROSS-REFERENCE TO RELATED APPLICATIONS

This application is a continuation of patent application Ser. No. 16/938,961, filed Jul. 25, 2020.

BACKGROUND OF THE INVENTION

The invention relates to a contactless delivery system and more particularly, a delivery locker having wireless communication interface and a disinfecting system.

DESCRIPTION OF THE RELATED TECHNOLOGY

In early 2020, most restaurants were forced to close their dining rooms because of the Covid-19 crisis. Restaurant operators and other sellers of goods increasingly turned to the sole off-premises channels such as delivery and carry-out. Some restaurants have encouraged all payments to be hands free and personal interactions to be minimal. Other measures include drop-off deliveries; increased frequency of bag cleaning; disinfecting high-touch surfaces; limiting the number of people inside an establishment and maintaining social distancing. Once food leaves a restaurant for delivery, customer visibility of order handling is lost. Maintaining the safety and the quality of the food is important, even when it's out of sight on the way to a diner. Excellent food safety practices, time management of cooked and holding food, proper packaging, tamper resistant seals, sanitation and customer guidance are all areas that have required greater attention for good delivery and pick-up.

Requirements have increased for food packaging to maintain hot and cold temperatures as long as possible and to uphold food quality. To help maintain temperatures, hot and cold foods may be packaged separately. Before pick-up, hot food may be held at 135 degrees F. or more and cold food may be held at 41 degrees F. or less for as long as possible. Limiting the time food is out of this temperature range to less than two hours is advisable. Restaurants must buffer the time of delivery into the suggested two-hour window where cold food is outside the temperature of less than 41 degrees F. and hot food is out of the temperature of more than 135 degrees F. Safety guidance includes suggestions to closed packaging using a tamper-proof seal. Some packaging solutions are: Adhesive seals on take-out bags that tear bag when opened, carryout containers with plastic tabs that break when food is accessed, tamper-evident labels, cartons with tamper-evident seals or adhesive strips or adhesive bands across the tops of lids and cups. Measures must be taken to ensure that a bag is secure enough to withstand possible movement and possible cross contamination during a transportation. Alternatively, double bag or secure everything together. In addition to tamper evident seals, labeling packages with the time and date of pick-up and including guidance such as heating or reheating instructions, if applicable has been suggested.

The concept of prepared meals to be eaten elsewhere dates back to antiquity. Archaeologists have found over 200 thermopolia service counters opening onto the street which provided food to be taken away in Pompeii. In the cities of medieval Europe, street vendors sold take-out food. In medieval London, street vendors sold hot meat pies, geese, sheep's feet, and French wine, while in Paris roasted meats, squab, tarts and flans, cheeses and eggs were available. A large strata of society would have purchased food from these vendors, but they were especially popular amongst the urban poor, who would have lacked kitchen facilities in which to prepare their own food. These vendors often had a bad reputation, often being in trouble with civic authorities reprimanding them for selling infected meat or reheated food. The "carry-out" food vendors of Norwich often defended themselves in court against selling such things as "pokky pies" and "stynkyng mackerelles". In Renaissance Turkey, many crossroads saw vendors selling "fragrant bites of hot meat", including chicken and lamb that had been spit roasted. Astec marketplaces had vendors that sold beverages such as atolli ("a gruel made from maize dough"), almost 50 types of tamales (with ingredients that ranged from the meat of turkey, rabbit, gopher, frog, and fish to fruits, eggs, and maize flowers), as well as insects and stews. After Spanish colonization of Peru and importation of European food stocks including wheat, sugarcane, and livestock, most commoners continued primarily to eat their traditional diets, but did add grilled beef hearts sold by street vendors. In 1707, after previous restrictions that had limited their operating hours, street food vendors had been banned in New York City. The Industrial Revolution saw an increase in the availability of take-out food. By the early $20^{th}$ Century, fish and chips was considered an "established institution" in Britain. The hamburger was introduced to America around this time. The diets of industrial workers were often poor, and these meals provided an "important component" to their nutrition. In India, local businesses and cooperatives had begun to supply workers in the City of Bombay (now Mumbai) with tiffin boxes by the end of the $19^{th}$ century. Despite a long history of problems with "unsafe" foods, there exists to this date a need for a more reliable food delivery system. This need has been heightened by the Covid-19 crisis.

Take-out food can be purchased from restaurants that also provide sit-down table service or from establishments specializing in food to be taken away. Providing a take-out service saves operators the cost of cutlery, crockery and pay for servers and hosts; it also allows many customers to be served quickly, without restricting sales by remaining to eat their food. Although once popular in Europe and America, street food has declined in popularity. In part, this can be attributed to a combination of the proliferation of specialized takeaway restaurants and legislation relating to health and safety. Many restaurants and take-out establishments offer drive-through that allow customers to order, pay for, and receive food without leaving their cars. The idea was pioneered in 1931 in a California fast food restaurant, Pig Stand Number 21. By 1988, 51% A of McDonald's turnover was being generated by drive-throughs, with 31% of all US take-out turnover being generated by them by 1990. Some take-out businesses offer prepared food for delivery, which usually involves contacting a local restaurant by telephone or on-line. In countries including Australia, Canada, India, Brazil, Japan, much of the European Union and the United States, food can be ordered on-line from a menu, then picked up by the customer or delivered by the restaurant or a third party delivery service. The industry has kept pace with technological developments since the 1980s, beginning with the rise of the personal computer and continuing with the rise of mobile devices and on-line delivery applications. Specialized computer software for food delivery helps determine the most efficient routes for carriers, track order and delivery times, manage calls and orders with PoS software, and other functions. Since 2008, satellite navigation tracking technology has been used for real-time monitoring of delivery vehicles by customers over the Internet. A restaurant can either maintain its own deliver personnel or use third parties who contract with restaurants to not only deliver food orders but also assist in marketing and providing order-taking technology. The field has seen rapid growth since the late 2000s with the spread of the smart phones and apps enabling customers to order from their mobile devices.

Retail food delivery is a courier service in which a restaurant, store, or independent food-delivery company delivers food to a customer. An order is typically made either through a restaurant or grocer's website or phone, or through a food ordering company. The delivered items can include entrees, sides, drinks, desserts, or grocery items and are typically delivered in boxes or bags. The delivery person will normally drive a car, but in bigger cities where homes and restaurants are closer together, they may use bikes or motorized scooters. Customers can, depending on the delivery company, choose to pay on-line or in person, with cash or card. Contactless delivery may also be an option. Other aspects of food delivery include catering and wholesale food service deliveries to restaurants, cafeterias, health care facilities, and caterers by foodservice distributors. Meal delivery orders are typically on demand, and intended to be eaten right away, and include hot, already-prepared food. Pizza delivery may be the largest meal delivery industry at the moment. Ordering for delivery usually involves contacting a local restaurant or chain by telephone or on-line. On-line ordering is available in many countries, where some stores offer on-line menus and ordering. Since 1995, companies such as Waiter.com have their own interfaces where customers order food from nearby restaurants that have partnered with the service. Meal delivery requires special technology and care, since the food items are already cooked and prepared, and can be easily damaged if dropped, tilted, or left out for long periods of time. Hot bags are often used to keep food warm. They are thermal bags, typically made of vinyl, nylon or Cordura, that passively retain heat.

Community-supported agriculture schemes work on a subscription box model, where a box of vegetables, diary product, fish, or meat is delivered periodically from a local vendor. Various meal kit delivery subscription services have started in Europe and North America since 2007. These typically have pre-measured ingredients designed for accompanying recipes. Grocery delivery companies will deliver groceries, or pre-made meals, and more to customers. The companies work with brick and mortar stores or their own line grocery items. These orders are typically larger and more expensive than normal meal deliveries and are often not meant to be eaten right away, rather they are to replace items someone has run out of, like flour or milk. They are almost always done on-line, and typically take at least one day to delivery, though some companies offer same-day delivery. Many delivery services are required to offer delivery within a couple of hours because frozen and fresh foods have to be delivered before they spoil. Grocery delivery differs from meal delivery in the sense that it is usually sent as a parcel through common mailing services like USPS or FedEx, if it is only non-perishables. Since non-perishables items are packaged before arriving at grocery stores, they can easily be repackaged and delivered to customers without any special care. Sometimes dry ice is added to keep perishable items fresh. Fresh and frozen foods complicate delivery, which is done, usually by store/provider employees or third-party services such as Instacart. The grocery delivery business has taken off, with hundreds of niche delivery companies springing up offering a variety of different services from weekly grocery restock to pre-planned, pre-measured family meals to make cooking easier. On-line retailer giants have hopped on-board too. Amazon-.com, for example, offers Amazon Fresh delivery service. Amazon purchased Whole Foods Market in 2017, and by 2018 Amazon had added Whole Foods items to its Prime Now service, for 2-hour delivery in certain markets. According to Forbes, grocery stores should deliver their own groceries to help prevent third party, part-time, non-store deliveries from becoming the 'face' or brand image of their local grocer. Limitations of having to pick and deliver groceries within a short period of time need to be remedied to allow for more flexibility to enable more deliveries to be more efficiently routed. Frozen and fresh food refrigeration units inside the store and the delivery vehicle, as well as lockable, consumer refrigeration boxes at the consumers home will be a solution that allows the groceries to be delivered at any time, further relieving delivery issues. This scenario will allow more local grocers to deliver with employees vs outside delivery services.

In a 2018 market study of restaurant delivery services, the global market for on-line ordered prepared food delivery was estimated at $94 billion and is estimated to grow at just over 9 percent a year, reaching $134.5 billion in 2023. The study defined the market as 1) "meals ordered on-line which are directly delivered by the restaurant, no matter if ordered via a platform (e.g., Delivery Hero) or a restaurant website (e.g. Domino's)"; 2) on-line meal orders and deliveries "both carried out by a platform" (Deliveroo, UberEATS, e.g.); 3) "on-line orders that are picked up in the restaurant" by the customer. It does not include phone orders. According to research conducted by the NDP Group, on-line restaurant ordering is growing 300% faster than dine-in traffic. "On-line ordering has started to become the norm, thanks to the convenience, accuracy, and ability to integrate payments." At scale, ubiquitous on-demand and subscription delivery of prepared food could potentially spell the end of cooking at home.

As the food delivery sector has grown, restaurants have turned to "ghost kitchens", also known as "cloud kitchen", to fill the need for inexpensive kitchen space to handle the increased volume. A ghost kitchen site will be purpose-built to be delivery-only and have separate areas of stoves, refrigeration, and storage space to accommodate food preparation teams of several different restaurants. As they are often located in less densely populated areas of a city, they also have parking areas for the delivery vehicles. Companies providing this service are often subsidiaries of the delivery companies. Ghost kitchens also allow for the creation of virtual restaurant brands—restaurants that exist only on-line, with no brick-and-mortar presence.

Ultraviolet germicidal irradiation (UVG or UVGI) is a disinfection method that uses short-wavelength ultraviolet (ultraviolet C or UV-C) light to kill or inactivate microorganisms by destroying nucleic acids and disrupting their DNA, leaving them unable to perform vital cellular functions. UVGI is used in a variety of applications, such as food, air, and water purification. UV-C light is weak at the Earth's surface since the ozone layer of the atmosphere blocks it. UVGI devices can produce strong enough UV-C light in circulating air or water systems to make them inhospitable environments to microorganisms such as bacteria, viruses, molds and other pathogens. UVGI can be coupled with a filtration system to sanitize air and water. The application of UVGI to disinfection has been an accepted practice since the mid-$20^{th}$ century. It has been used primarily in medical sanitation and sterile work facilities, increasingly, it has been employed to sterilize drinking and wastewater since the holding facilities are enclosed and can be circulated to ensure a higher exposure to the UV. In recent years, UVGI has found renewed application in air purifiers. In 1878, Arthur Downes and Thomas P. Blunt published a paper describing the sterilization of bacteria exposed to short-wavelength light. UV has been a known mutagen at the cellular level for over 100 years. The 1903 Nobel Prize for Medicine was award to Niels Finsen for his use of UV against lupus vulgaris, tuberculosis of the skin. Using UV light for disinfection of drinking water dates back to 1910 in Marseille, France. The prototype plant was shut down after a short time due to poor reliability. In 1955, UV water treatment systems were applied in Austria and Switzerland; by 1985 about 1,500 plants were employed in Europe. In 1998, it was discovered that protozoa such as cryptosporidium and giardia were more vulnerable to UV light than previously thought; this opened the way to wide-scale use of UV water treatment in North America. By 2001, over 6,000 UV water treatment plants were operating in Europe. Microorganisms have low protection against UV and cannot survive prolonged exposure. A UVGI system is designed to expose environments such as water tanks, sealed rooms and forced air systems to germicidal UV. Exposure comes from germicidal lamps that emit germicidal UV at the correct wavelength, thus irradiating the environment. The forced flow of air water through this environment ensures exposure. The effectiveness of this form of disinfection depends on-line-of-sight exposure of the microorganisms to the UV light. Environments where design creates obstacles that block the UV light are not as effective. In such an environment, the effectiveness is then reliant on the placement of the UVGI system so that line of sight is optimum for disinfection. Dust and films coating the bulb lower UV output. Therefore, bulbs require periodic cleaning and replacement to ensure effectiveness.

U.S. Pat. No. 10,424,143, the disclosure of which is expressly incorporated by reference herein, relates to package delivery and collection systems comprising assemblies of automated lockers which are monitored and controlled by a central computer system. Each locker door is secured by a lock which can be locked and unlocked electronically responsive to validation of an access request received via a local user interface, so that packages can be securely deposited and collected by authorized users of the system.

According to U.S. Pat. No. 10,424,143, automated locker systems can be used for example as a last mile delivery system for consumer goods ordered online, wherein each package is delivered by authorized delivery personnel and collected by a consumer using a one-time collection code. Alternatively, for example, a block or bank of lockers might be a centralized station to collect, exchange and return goods. Alternatively, an automated locker assembly might be located in a supermarket or the like for use by its customers to collect individual grocery orders which are picked and packed by the supermarket staff.

WO2014/125243A1, the disclosure of which is expressly incorporated by reference herein, discloses a system, in which each locker assembly is controlled by a local control unit which communicates with the central computer system via a direct data link and via handheld wireless communication devices carried by delivery personnel. The local control unit functions autonomously based on the most recent set of instructions received from the central computer system.

By grouping together a plurality of lockers into an automated locker assembly, it is possible to control each of the lockers via a sophisticated local control system and user interface including barcode scanning and other functionality and a data connection to a central computer system located remotely from the locker assembly. The operation of all of the lockers can then be monitored and controlled centrally so that they can function effectively as part of a wider logistics network in which a package can be tracked to the point of delivery, and the customer then notified and authorized to perform the collection.

SUMMARY OF THE INVENTION

There exists a great need for a contactless delivery system, particularly for prepared food that enhances the safety of an order and gives customers enhanced confidence in the safety of an order. This may be accomplished by a locker system with contactless opening, UV disinfecting, status reporting, and security features. According to an advantageous feature, a user will have confidence that a locker remains continuously closed and sealed from the time an order is loaded into a delivery locker until the locker is opened by the user, and has been disinfected to reduce or eliminate any microorganism contaminant on the food containers.

According to an advantageous feature, it is an object to provide a smart contactless delivery locker. It is a further object to provide a contactless delivery locker with disinfecting capabilities. It is a further object to provide a contactless food delivery locker which may be portable so as to be useful for food delivery services. It is an object to provide a delivery locker which may be suitable for mobile food delivery services such as UberEATS®. It is a further object to provide a disinfecting contactless delivery system which may include one or multiple food lockers in a locker bank. It is a further object to provide a delivery locker which may have touchless opening features. It is a further object to provide a system that can enhance the safety of take-out food and enhance customer confidence in the safety of take-out food, whether by carry-out or delivery. It is a further object to provide a food delivery locker which may have environmental insulation of environmental controls such as heating, cooling, and/or freezing. These and other objects may be obtained by using a stackable locker. The locker housing may be constructed from a polyurethane or expanded polypropylene. The locker may have an on-board power supply and may have smart capabilities to allow a customer to monitor the status of the locker prior to its delivery, including loading time, location, food or item availability, temperature, disinfecting system operation and locker identification.

According to an advantageous feature, the locker may include a wireless interface such as Bluetooth, or cellular, M2M, BLE, Zigbee, Wi-Fi, LPWAN, LTE, or other remote communications capabilities. The locker may be provided with GPS receiver so as to facilitate location tracking or location reporting.

The locker may be in the form of a box with a door. The box may be of any suitable material such as expanded polypropylene. The door may be hinged, or pivot mounted or arranged to slide in a suitable recess in the box housing. The door or the box housing may be provided with a viewing window.

The locker may include an indicator or multiple indicators for visual communications. The indicators may be one or more lights such as an LED or LED'Ss and/or a suitably sized display. The indicator may be provided to visually indicate status such as loaded, ready, cleaning, heating, cooling, etc. In addition, the indicator may display a locker ID and/or a customer name, or ID. The indicator may also include a representation of temperature time or a lapsed time since being filled. A number of other relevant information may be provided through the display. In addition, the opportunity exists for the display to provide digital signage for presenting advertising or other information.

The locker may include a lock for securing the door in a closed position. The lock may be released to allow the locker door to be opened either manually or by some contactless mechanism.

A digital controller such as a microprocessor based controller may be provided to control operation of the locker. The controller may be on-board the locker or may be remotely located. The system may be designed for an operator of the locker to load the locker with one or more items to be collected by another such as a customer. Advantageously, the operator may be a restaurant, kitchen, or a delivery service which loads the locker with an order such as food order. The order may be placed by a customer using an on-line ordering system or, according to some other process. For example, regular inventory supply or meal delivery may be scheduled or established without requiring an immediate customer order. The system may notify the operator of the item or items to load into the locker and the system may notify a user or delivery service that the item is ready to be collected or the locker is to be delivered.

The system allows for a stationary deployment of either an individual locker and/or a bank of lockers, for use in delivery without personal interaction or contact between fulfillment personal and a customer. A customer or user may collect the item or items loaded into the locker. The system may include a wireless communication capability whereby a user may trigger opening of a locker at an appropriate time using a mobile computing device such as a smart phone running an appropriate application program. The software may be set-up as a web-application or may be distributed between a server, the locker, and the user device. The precise location or distribution of the software is not critical.

There are several features which may be incorporated into the delivery locker depending on the system requirements.

In order to secure the payload within the locker until the user collects the content, a lock is provided to secure the door to the locker. As discussed previously, the lock may be remotely operated so that a user may use an app to release the electronic lock and open the door. The door may be manually operated or automatically opened upon release of the lock. The user control may be through direct instructions through an app residing on a smart device or another mechanism such as proximity sensor or optical scan.

For lockers which will be used for mobile delivery, the locker may be provided with location sensing or reporting capabilities. The location sensing or reporting may be by an IoT device and any location services provided, such as an IOS, Android, or JAVA based devices; although, the system is not limited to the operating systems.

The locker may be provided with a temperature sensor, a door sensor, and a clock or timer so that the conditions within the locker may be reported to a user or operator. The user or operator may take certain actions on the basis of the information provided. For example, a user or operator may determine that temperature sensitive contents are spoiled if exposed to certain temperatures over certain periods of time.

The controller and operation of the box may be provided with security features to control access to the locker and to secure communications of information relating to the locker conditions.

The locker may be provided with heating and/or cooling capabilities which may be used to maintain the environment within the locker as desired. For example, a locker which is utilized for delivery of ice cream should be kept below a predetermined temperature, which may be maintained using cooling systems such as refrigeration.

The locker may be provided with a disinfecting system, for example, a UV radiation system which is suitable to emit sufficient ultra-violet energy/wavelengths to disinfect irradiated surfaces.

The locker may be provided with an on-board power supply or be docked and connected to a power source. An on-board power supply with a battery may be suitable for a locker module which will be moved. The locker may be collected from a locker loading station and transported to the location of the user or other intermediate location.

The locker may be provided with structures designed to allow multiple lockers to be stacked in a more secure fashion. It is an object to provide a take-out food delivery and carry-out experience with greater safety to the customer.

It is an object to provide a more efficient way of distributing goods through an automated locker system.

U.S. Pat. No. 10,424,143 discloses a package delivery and collection system for use with a plurality of wireless communication devices communicating via a communications network. According to an advantageous embodiment, the system may be improved and adapted to be an advanced delivery system for contactless restaurant take-out service including carry-out (customer pick-up) and delivery (transport) to a remote customer location.

The system may comprise one or more locker modules or a plurality of locker modules arranged in a locker bank. The locker modules may include a door and a lock unit, the lock unit including a lock, the lock being operable to lock the door to secure a payload inside the locker and to unlock the door to permit the payload to be removed from the locker.

The system may work with a sever linked to a locker controller and a user interface connected by a wireless communication channel. Each locker may include a lock unit with a processor and a wireless communication interface for communicating with a user interface, for example a personal communication device for example a smart phone. A controller for the locker may be a processor configured to receive an access request from the user's personal communications device to validate the access request, and responsive to successful validation of the access request, to unlock the locker door to allow access to the locker. The access request and other communications between a personal communications device and a locker module controller may be through any communications channel, preferably wireless. For example, the communication channel may be a short range wireless channel like a Bluetooth channel of a long-range wireless channel like cellular or M2M cellular. The channel may be Wi-Fi or long-range Wi-Fi. The channel may be direct between the personal communications device and the locker module or indirect, between the personal communications device through a server connected directly or indirectly to both.

The communication may be active, by a two-way electronic communication protocol like TCP/IP or by one-way communications, for example the locker module may have an optical scanner and the personal communications device may display a QR code and communications from the locker module to a user may be by information on a display or other indicators. Access may also be controlled by a proximity sensor. The locker module may be opened automatically or may prompt a customer to authorize opening the module when the user's personal communication device is in the immediate proximity of the locker bank or locker module. Proximity sensing technology itself is well known and may be accomplished directly by determining proximity of devices or indirectly by determining distance between locations of devices or by determining distance of devices in a fixed frame of references, such as by Wi-Fi triangulation in a Wi-Fi geolocation (positioning) system.

A method of operating the contactless delivery system may include the steps of receiving, by the controller, via the communication channel, an access request from a program running on a personal communication device, which may be a device proximate to the lock unit of the locker module; validating, by the processor, the access request; and responsive to at least successful validation of the access request, initiating, by the controller, an event including unlocking the locker module door to allow access to the locker module. The access request may be based on an enabling message generated by a server and transmitted via a communications network in modified or unmodified form, directly or indirectly to the personal communication device, the server being arranged to generate the enabling message for the lock unit.

Advantageously, the user interface functionality conventionally provided by a local control unit and dedicated data link may be provided instead by the program in combination with the touchscreen, keypad, barcode scanning and communications functions conventionally built into a personal communication device, such as a smart phone, on which the program is running. By downloading and installing the program as an app, a consumer may access the lockers using a simple user interface which is generated by the program on the display of their device in combination with the touchscreen or keypad. The program may be configured to generate the access request automatically based on the enabling message responsive to a simple input from the user, such as pressing a button marked "collect package" or the like on their touchscreen display, and without requiring the user to remember or type in any codes or the like, so that the system is more convenient in use.

A collection ID might be in the form of a barcode which may be sent to the customer, to be printed, or displayed on a mobile phone or other device. The locker module controller may provide status information to a user prior to or at the time of collection of the payload. The status information may include one or more of: order ready time; door closed time(s); door open time(s); door secured flag, to indicate that the door has not been opened over a period of interest which may be a period commencing when the payload is loaded, the period commencing when the UV disinfection cycle is initiated, or another period; UV disinfecting cycle status; temperature; elapsed time or other information.

Further and more specific objectives, optional features and advantages will become evident from the various illustrative embodiments which will now be described, purely by way of example and without limitation to the scope of the claims, and with reference to the accompanying drawing, which shows various elements of a contactless delivery system.

In general, the features described may be applied as appropriate and mutatis mutandis to any of the embodiments.

Various objects, features, aspects, and advantages of the present invention will become more apparent from the following detailed description of preferred embodiments of the invention, along with the accompanying drawings in which like numerals represent like components.

Moreover, the above objects and advantages of the invention are illustrative, and not exhaustive, of those that can be achieved by the invention. Thus, these and other objects and advantages of the invention will be apparent from the description herein, both as embodied herein and as modified in view of any variations which will be apparent to those skilled in the art.

DETAILED DESCRIPTION OF THE PREFERRED EMBODIMENT

Figure 1:
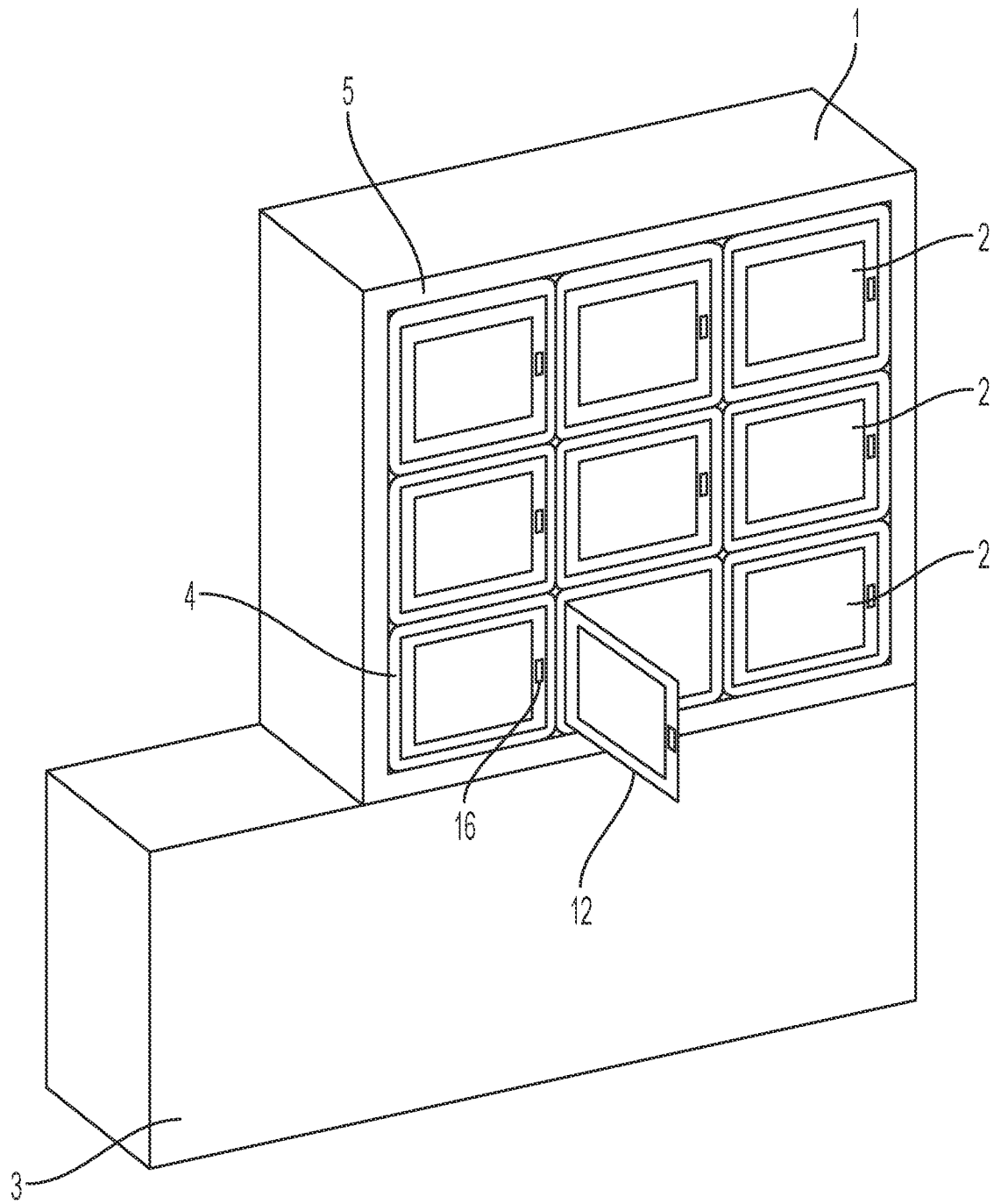
FIG. 1 shows a locker bank.

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, between the upper and lower limit of that range and any other stated or intervening value in that stated range is encompassed by the range of values. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

A locker or bank of lockers may be provided for contactless transfer of carry-out orders from a restaurant operator to a customer. The customer may have a wireless personal communication device for communicating with the operator and for remotely operating a locker module.

Each customer may use their own personal communication device which may run a collection program, which may be downloaded and installed as an app on their device, which is configured to simplify the process of collecting a single package from a single locker.

A customer may register with an operator. The operator may be a restaurant or other vendor, or an ordering service. The ordering service may include delivery transportation. Once an order is placed and communicated to an operator, the operator prepares the order for placement in a locker module as the "payload". For a restaurant, the payload will be the food specified by the order. The locker may be delivered (transported) as requested by the customer or may be held at the operator facility for carry-out. The time that the locker is loaded and closed may be recorded and reported to the customer. The status of the door may be monitored and a change in status may be reported. In this way, a customer may ascertain when and if the door is opened. This will engender confidence in the customer that once the locker is loaded, it has not been opened at any time prior to being opened by the customer. In addition to the monitor, or instead of the monitor, the door may be locked. The customer will be able to unlock the door on arrival of delivery. The ability of a third party transporter to open the locker module and potentially contaminate the payload without knowledge of the customer is thereby limited. Once the payload is place in the locker module, a UV disinfecting light can disinfect the surface of the payload exposed to the UV light. This is intended to reduce or eliminate any contaminants on the surfaces exposed in the UV radiation.

FIG. 1 shows a locker bank 1 with nine lockers 2. The lockers 2 may be arranged on a stand 3. The lockers may be integrally constructed in the bank or may be stacked locker modules 4. One of the locker modules 4 is shown with an open door 12. The lockers 2 may be integral parts of the locker bank 1 or may be modular. In the case of a modular locker, they may be fixed in the locker bank 1 or may be removable. The locker bank 1 may include a frame 5 with the lockers 2 arranged in the frame.

Figure 2:
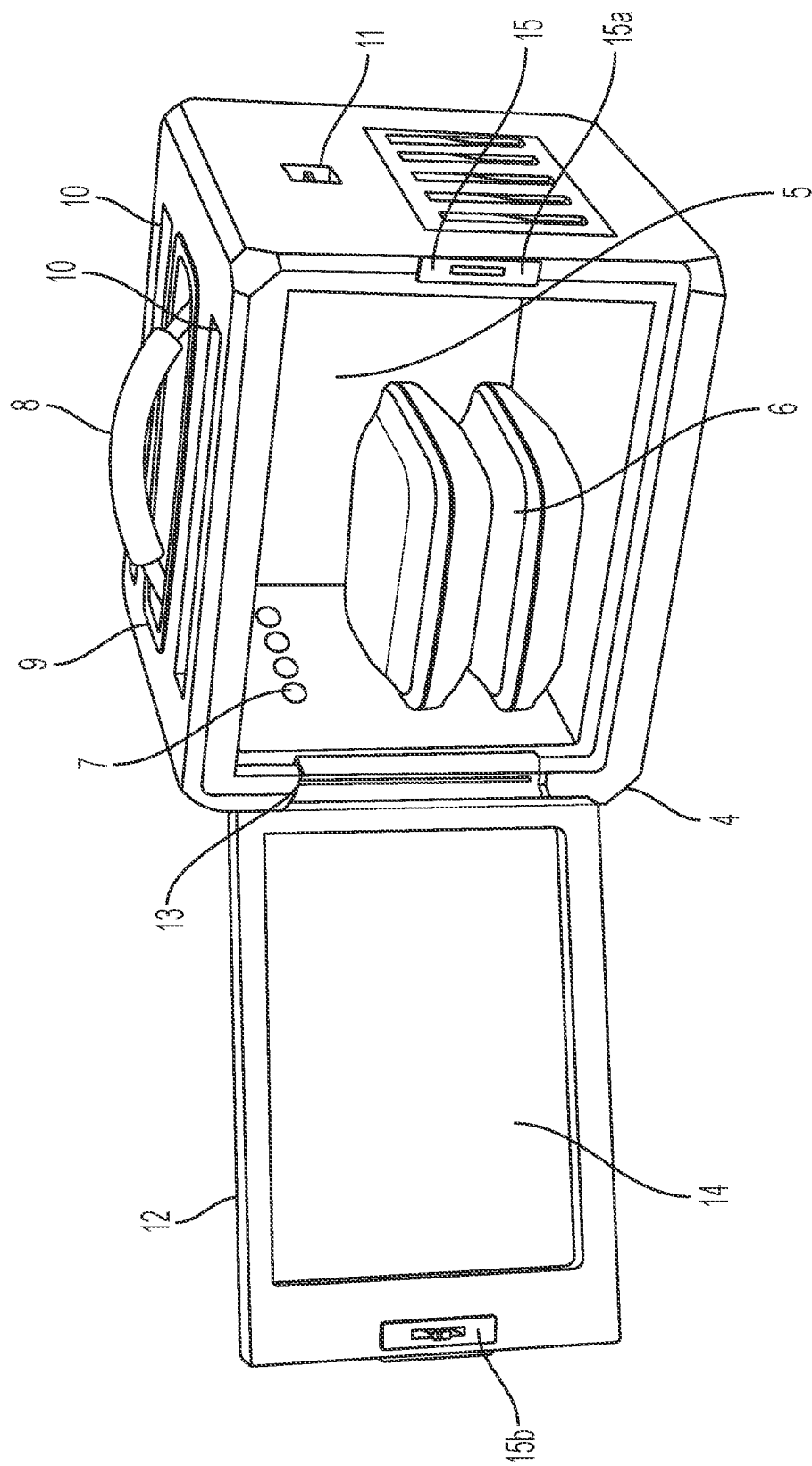
FIG. 2 shows a locker module.

FIG. 2 shows a locker module 4. The locker module 4 defines a storage space 5 which is suitable for containing a payload 6, for example, one or more prepared food containers. One or more light sources 7 may be mounted to irradiate the payload 6. The light sources 7 may be placed on any or all interior surface of the storage space 5 (walls, door, ceiling, and/or floor). The light sources 7 may be LED's, lamps, or a combination of LED's and lamps. The light sources 7 may provide visible light and/or UV-C in the storage space 5.

One or more of the light sources 7 may generate UV germicidal irradiation (UVGI) within the lockers 2. The UV-C light sources 7 may be distributed to bathe a payload in UV-C radiation. The interior walls of the storage space may include one or more reflecting, scattering, and diffusing surfaces or a combination thereof to enhance the coverage of the surface area of the payload 6 with UV-C.

A locker module 4 may include a handle 8 which may retract into a handle recess 9. UV-C LEDs or other light sources (not shown) may expose the handle to UV-C. The outer shell of the locker module 4 may include stacking recesses 10 to mate with stacking protrusions (not shown) on an opposed surface of a second locker module. Conveniently stacking recesses 10 may be located on a top surface of a locker module 4 and corresponding stacking protrusions may be on a bottom surface of the locker module 4. The locker module 4 may be provided with anchors 11 to allow for connecting carrying straps or mounting.

A door 12 may be pivot mounted on one or more hinges 13. The door may have window 14. The window 14 may be glass, a display, or a see-through display.

The locker module 4 may be provided with catch, latch or lock referred to as a closure mechanism 15. The closure mechanism may include a component 15a mounted in the frame of the locker module 4 and a component 15b mounted on the door 12 that cooperates with component 15a. The closure mechanism 15 may be manual, but advantageously is remotely operated by a customer or operator. The closure 15 may also include a mechanical release 16 shown in FIG. 1 and a UV-C light source(s), providing UVGI on the mechanical release 16. The closure mechanism may include a lock, a sensor, and/or a pop-open capability when remotely activated and may include damping functions or automated functions and structure.

Figure 3:
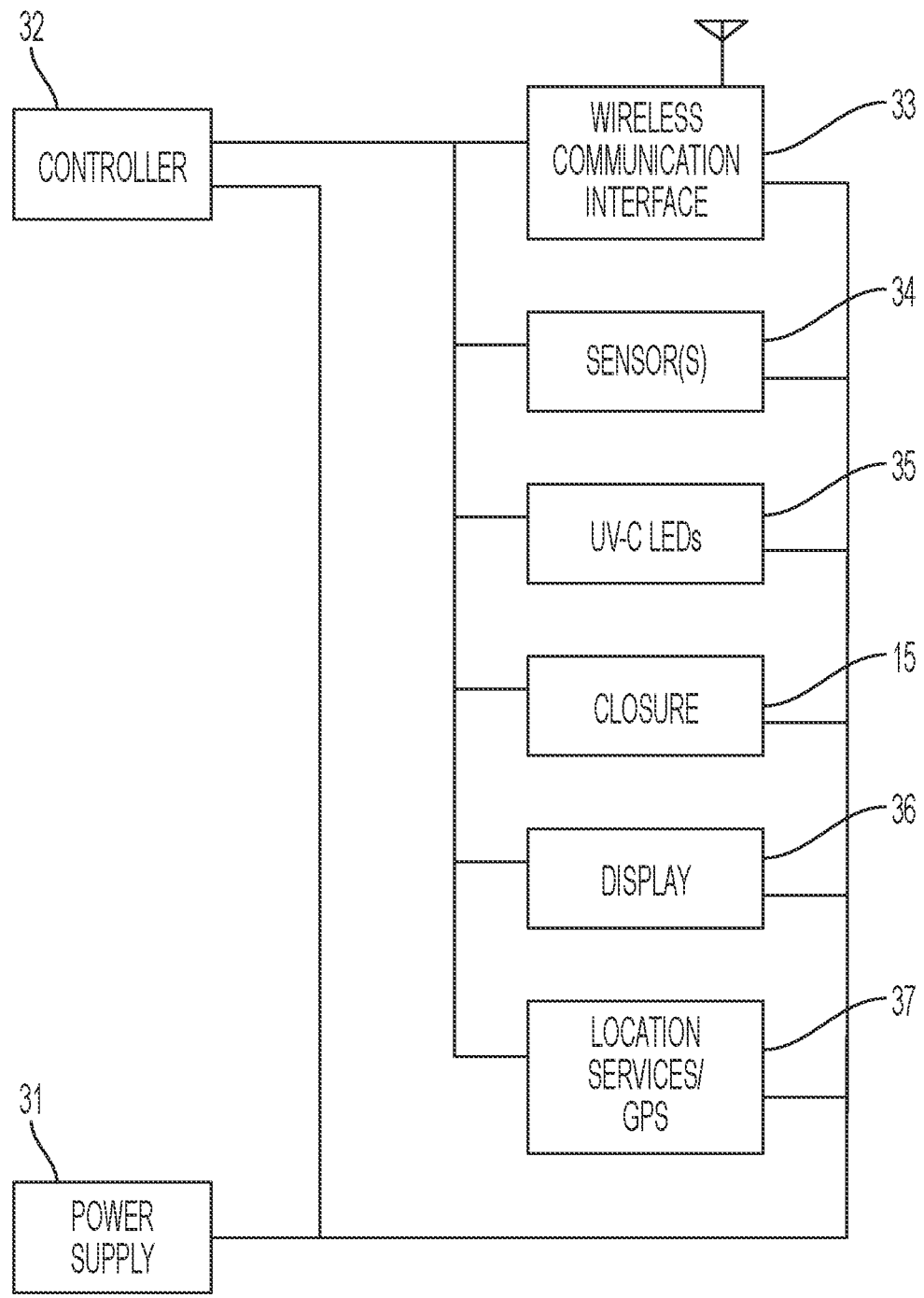
FIG. 3 shows a schematic of the access control features.

FIG. 3 shows a schematic of the access control features of the locker module 4.

The locker module 4 may include a power supply 31 such as a rechargeable or replaceable battery, a controller 32, such as a processor with suitable memory and programming. The controller 32 may be connected to a wireless communication interface 33, for example, a Bluetooth or cellular interface, and the closure mechanism 15. One or more sensors 34 may also be provided and connected to the controller 32, for example, to sense the position or status of the locker module door 12 or the temperature within the locker module 4. The controller may also be connected to control the UV-C LED's 35 and display 36 mounted on the locker module 4.

The closure mechanism 15 may include a lock unit and may include a lock, such as a solenoid operated bolt or a motorized bolt or any other element which is mechanically or magnetically operable under control of the processor to be engageable and disengageable with the frame to lock and unlock the door, optionally also to open and close the door, such as by engaging a sloping cam surface on the frame to draw the door from a slightly open position to a fully closed position so as to permit contactless loading or unloading of the payload 6. A mechanical override may be provided by which the door can be released using a handle or suitable tool. The sensor 34 (if present) may be incorporated into the closure mechanism 15 or lock, e.g. to sense the position of the locking element.

The door may be provided with a self-closing and/or self-opening device. The self-closing and/or self-opening device may be powered by energy stored in the battery or stored mechanically (e.g. using a spring, a pneumatic cylinder, or the like). The self-closing and/or self-opening device may be incorporated into closure 15 and may be controlled by controller 32.

The controller 32 may be configured to transmit the status of the sensor closure and/or UV-C LED's directly or indirectly to a user's personal communication device i.e. smart phone or other device running a suitable app using short-range (page 35 of the contactless locker delivery system application).

Figure 4:
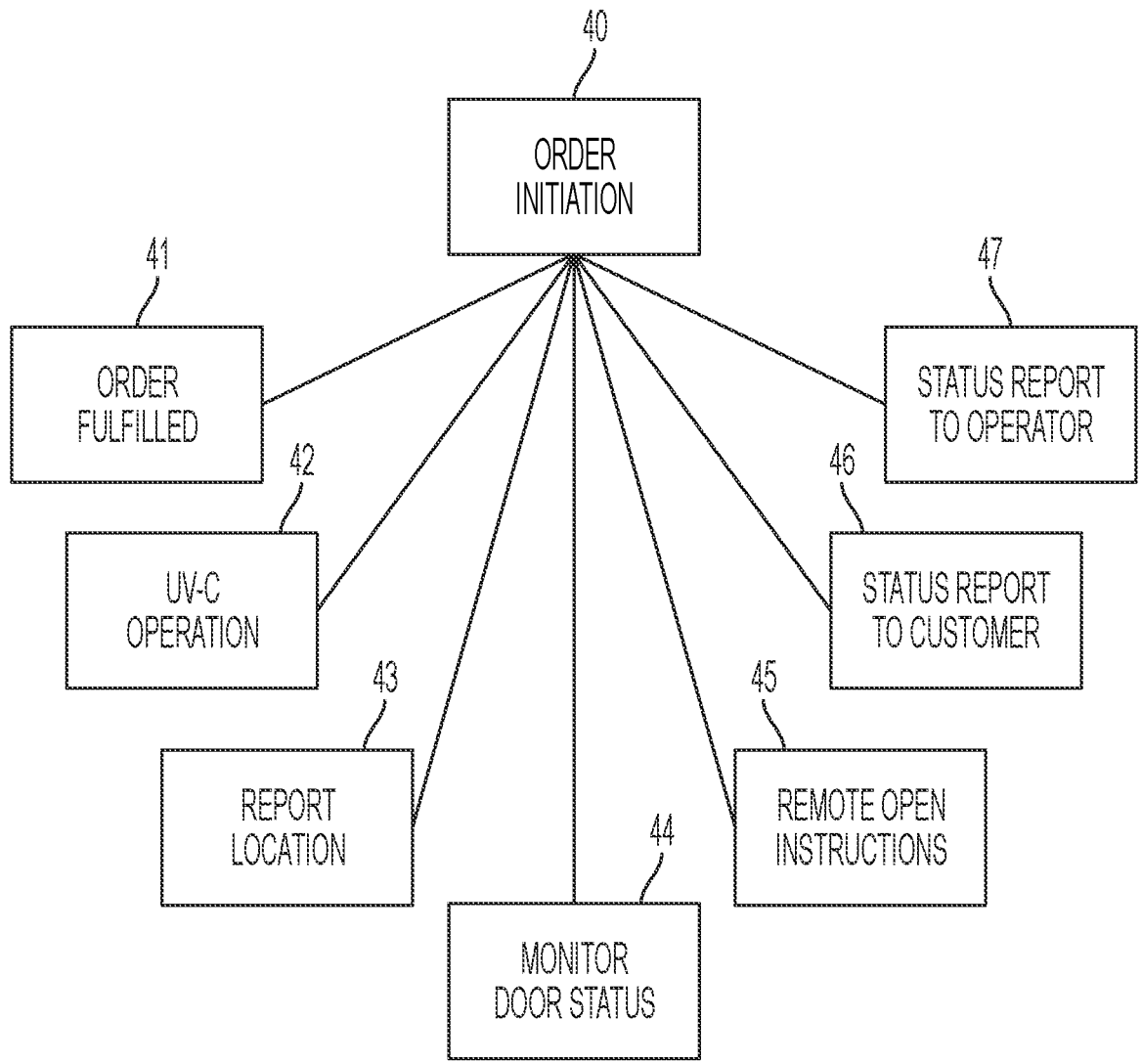
FIG. 4 shows an embodiment of a contactless delivery operation.

FIG. 4 shows an embodiment of a contactless delivery operation using the locker module 4. The locker module 4 may remain stationary at the operator facility (restaurant) or be delivered to a customer. An order fulfillment system may be utilized in conjunction with the contactless delivery system, for example, to take orders, advise a customer of order status, manage payments, and/or dispatch delivery service. These functions are compatible with the use of the contactless delivery system but need not be part of the system. The system may provide an order fulfillment message 41. The message may be generated when an operator indicates that the order is fulfilled or may be generated in advance to communicate the anticipated fulfillment time. In a static location system, the message may advise the customer when the order is ready for pick-up. In a mobile delivery system, the customer may be advised when the locker module 4 is left at the delivery location or when to anticipate delivery. In this manner, it is possible for the customer to not actually be in contact with anyone from the operator facility, and in a mobile situation, not be in contact with the delivery service provider.

Once the payload is placed in the locker, the disinfecting cycle may be activated at step 42. The disinfecting cycle may commence by activation of the UV-C LED's at the time of fulfillment and may continue for a time or until being deactivated by a user. In such case, the UV-C LED's may be deactivated when the door 12 is unlocked or opened.

For operation with a delivery service, the locker may include a GPS 37 or other location service element. With a delivery service, the GPS may report to the customer the location of the locker, thus reducing or eliminating the need for the order fulfilled message 41 to indicate the delivery of the locker manual. The locker module 4 may use a wireless communication interface like IOT or cellular M2M to report on its own location and the system may advise the user/customer when the locker module reaches the user location.

The door closure 15 may be locked once the payload is placed into the locker manual. The sensor may determine if the door is opened. The customer will be able to ascertain whether the door has been opened at any point, including after initiation of a UV-C disinfecting cycle, since being loaded by the operator, or if the door had not been opened. This is accomplished by monitoring door status 44 by reporting a change detected by the sensor or a closure 15 opening operation.

The user may simply rely on the closed or locked status of the door without further monitoring if the user can be confident that the locker module lock has not been tempered with. Upon arrival of the customer at the locker module location for pick-up or upon delivery of the locker module 4 to the customer, the customer may initiate a door open operation. This may be done in a contactless fashion by issuing remote open instructions 45 from the user's personal communications device. This can be done by an app on a user personal communication device such as a smart phone. The app may issue Bluetooth instructions to the locker module 4 for user-to-module communications, or in the event the module is connected to a network, the user may issue instructions over a network. In either case, the user will have the capability of contactless operation of the locker module door 12.

The status may be reported 46 to the customer through a personal communication device or communications or over the network for a network connected device. A door closure operation report 47 can advise the operator of the availability of the locker module 4 for another customer, the availability of the locker module 4 may initiate a disinfecting cycle before being available to another customer or for pick-up by a delivery service. The closure the locker module door may trigger activation of the UV-C LED's for another disinfecting cycle in case the customer unloading of the locker module introduced any microorganism contamination.

It should be appreciated that the combined features of the secured storage contactless delivery UV disinfecting and status monitoring is unique and solves a long felt need in take-out food delivery as contaminated foods have historically been a problem for take-out food delivery and the Covid-19 crisis has eliminated or at least reduced the ability for dine-in service and increased the consumer apprehension of the safety of take-out.

The techniques, processes and apparatus described may be utilized to control operation of any device and conserve use of resources based on conditions detected or applicable to the device.

The system is described in detail with respect to preferred embodiments, and it will now be apparent from the foregoing to those skilled in the art that changes and modifications may be made without departing from the invention in its broader aspects, and the invention, therefore, as defined in the claims, is intended to cover all such changes and modifications that fall within the true spirit of the invention.

Thus, specific apparatus for and methods of have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A contactless delivery locker system comprising:
    a plurality of contactless delivery lockers arranged in a bank of lockers wherein each locker includes a locker display and the system is configured to display an image on said locker display to provide a locker identification in response to detection of a personal communication device associated with said locker, and wherein each locker includes at least:
    i) a locker housing;
    ii) a locker door fitted to said locker housing having said locker display arranged on said locker door wherein said locker display is sized to cover a significant portion of the locker door and sized to be used for digital signage;
    iii) a disinfecting system arranged to disinfect locker content; and
    iv) a remotely actuable lock arranged to secure said door in a closed position and actuable to release said door;
        a controller associated with said remotely actuable lock configured to actuate said lock; and
        a wireless interface connected to said controller and configured to receive a command to actuate said remotely actuable lock to release said locker door; and
        wherein said controller operates to control actuation of said remotely actuable lock to release said locker door upon detection of said command to actuate said remotely actuable lock and release said locker door, wherein said controller is configured to show digital signage and a customer ID on said locker display, and wherein said controller is configured to report lock status information after completion of a disinfecting cycle to a user to confirm if a locker has been opened between completion of a disinfecting cycle and a user operation to open said locker door.

2. The contactless delivery locker system according to claim 1, wherein said disinfecting system further comprises a UV-C light source.

3. The contactless delivery locker system according to claim 2, wherein said UV-C light source is one or more UV-C LEDs.

4. The contactless delivery locker system according to claim 3, wherein said remotely actuatable lock further comprises an automatic door opener.

5. The contactless delivery locker system according to claim 4, wherein said controller is configured to generate a status report and provide said status report to said wireless interface for transmission.

6. The contactless delivery locker system according to claim 5 further comprising location-based services connected to said controller.

7. The contactless delivery locker system according to claim 6 further comprising a GPS receiver connected to said location-based services and said status report includes a location report.

8. The contactless delivery locker system according to claim 5, wherein said disinfecting system further comprises a timer connected to said UV-C light source.

9. The contactless delivery locker system according to claim 8, wherein said status report includes a report of operation of said disinfecting system.

10. The contactless delivery locker system according to claim 5 further comprising a temperature sensor and said status report includes sensed temperature within said locker housing.

11. The contactless delivery locker system according to claim 1, wherein said locker display is a see-through display mounted in said locker door.

12. The contactless delivery locker system according to claim 1, wherein said locker door is pivot mounted to said locker housing.

13. The contactless delivery locker system according to claim 1, wherein interior surfaces of said locker housing includes reflective surfaces.

14. The contactless delivery locker system according to claim 1, wherein interior surfaces of said locker housing include light scattering surfaces.

15. The contactless delivery locker system according to claim 1 further comprising a handle connected to said locker housing.

16. The contactless delivery locker system according to claim 15, wherein said disinfecting system further comprises a UV-C light source to provide UVGI to said handle.

* * * * *